(12) United States Patent
Rosentreter et al.

(10) Patent No.: US 7,109,218 B2
(45) Date of Patent: Sep. 19, 2006

(54) SUBSTITUTED 2-THIO-3,5-DICYANO-4-PHENYL-6-AMINOPYRIDINES AND THE USE OF THE SAME

(75) Inventors: Ulrich Rosentreter, Wuppertal (DE); Thomas Krämer, Wuppertal (DE); Mitsuyuki Shimada, Nara (JP); Walter Hübsch, Wuppertal (DE); Nicole Diedrichs, Wuppertal (DE); Thomas Krahn, Hagen (DE); Kerstin Henninger, Wuppertal (DE); Johannes-Peter Stasch, Solingen (DE); Ralf Wischnat, Leverkusen (DE)

(73) Assignee: Bayer HealthCare AG, Leverkusen (DE)

( * ) Notice: Subject to any disclaimer, the term of this patent is extended or adjusted under 35 U.S.C. 154(b) by 0 days.

(21) Appl. No.: 10/497,120

(22) PCT Filed: Nov. 28, 2002

(86) PCT No.: PCT/EP02/13432

§ 371 (c)(1),
(2), (4) Date: Jun. 2, 2005

(87) PCT Pub. No.: WO03/053441

PCT Pub. Date: Jul. 3, 2003

(65) Prior Publication Data

US 2005/0227972 A1    Oct. 13, 2005

(30) Foreign Application Priority Data

Dec. 11, 2001 (DE) .......................... 101 60 661
Aug. 21, 2002 (DE) .......................... 102 38 113

(51) Int. Cl.
*C07D 417/12* (2006.01)
*A61K 31/4418* (2006.01)

(52) U.S. Cl. ............ 514/332; 514/342; 514/344; 546/255; 546/269.7; 546/287

(58) Field of Classification Search ............ 514/332, 514/342, 344; 546/255, 287, 269.7
See application file for complete search history.

(56) References Cited

FOREIGN PATENT DOCUMENTS

| WO | 0125210 | 4/2001 |
|---|---|---|
| WO | 0270485 | 9/2002 |
| WO | 0279195 | 10/2002 |
| WO | 0308384 | 1/2003 |

OTHER PUBLICATIONS

Klotz, et al., "Comparative pharmacology of human adenosine receptor subtypes-characterization of stably transfected receptors in CHO cells", Springer-Verlag, 1998.
Olah, et al., "Cloning, Expression, and Characterization of the Unique Bovine A1 Adenosine Receptor", Journal od Biological Chemistry, 267(15), 10764-10770, 1992.
Poulsen, et al., "Adenosine Receptors:New Opportunities for Future Drugs", Bioorganic & Medicinal Chemistry, 6, 619-641, 1998.
Dyachenko, et al., "New Route to 6-Amino-4-aryl-3,5-dicyano-pyridine-2 (1H)-thiones", Journal of Organic Chemistry, 33 (7), 1014-1017, 1997.
Dyachenko, et al., "Michael Reaction in Synthesis of 6-Amino-4-(4-Butoxyphenyl)-3,5-Dicyanopyridine-2(1H)-thione", Chemistry of Heterocyclic Compounds, 34(2), 188-194, 1998.
Quintela, et al., "Synthesis, antihistaminic and cytotoxic activity of pyridothieno-and pyridodithienotriazines", J.Med.Chem., 33, 887-897, 1998.
Torgoman, et al., "Nitriles in Heterocyclic Synthesis: The reaction of 2-Thiocarbamoyl Cinnamonitriles with Active Methylene Reagents", Cairo University, 42b, 107-111, 1987.
Kambe, et al, "Synthetic Studies Using a-B-Unsaturated Nitriles:facile Synthesis of Pyridine Derivatives", Communications, 531-533, 1981.
Elnagdi, et al., "Studies with Polyfunctionally Substituted Heterocycles", Cairo University, 47b., 572-578, 1992.
Muller, et al., "Adenosine Receptor Antagonists:Structures and Potential Therapeutic Applications", Current Pharmaceutical Design, 2, 501-530, 1996.

*Primary Examiner*—Zinna N. Davis
(74) *Attorney, Agent, or Firm*—Susan M. Pellegrino

(57) ABSTRACT

Compounds of the formula (I)

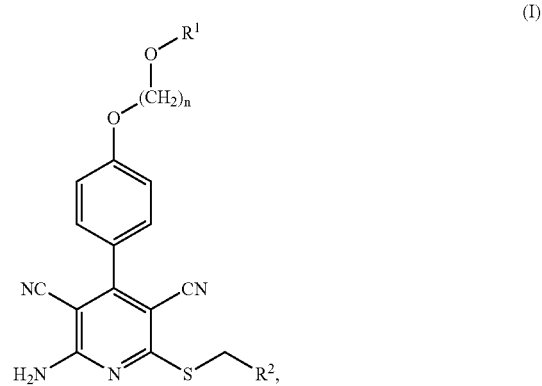

a process for their preparation and their use as medicaments are described.

8 Claims, No Drawings

SUBSTITUTED 2-THIO-3,5-DICYANO-4-PHENYL-6-AMINOPYRIDINES AND THE USE OF THE SAME

The present invention relates to substituted 2-thio-3,5-dicyano-4-phenyl-6-amino-pyridines, to a process for their preparation and to their use as medicaments.

Adenosine, a nucleoside consisting of adenine and D-ribose, is an endogenous factor having cell-protective activity, in particular under cell-damaging conditions with limited oxygen and substrate supply, such as, for example, in the case of ischaemia in various organs (for example heart and brain).

Adenosine is formed intracellularly as an intermediate during the degradation of adenosine-5'-monophosphate (AMP) and S-adenosylhomocysteine, but it can be released from the cell, in which case it acts as a hormone-like substance or neurotransmitter by binding to specific receptors.

Under normoxic conditions, the concentration of free adenosine in the extracellular space is very low. However, under ischaemic or hypoxic conditions, the extracellular concentration of adenosine in the affected organs is increased dramatically. Thus, it is known, for example, that adenosine inhibits platelet aggregation and increases the blood supply to the coronary arteries. Furthermore, it acts on the heart rate, on the release of neurotransmitters and on lymphocyte differentiation.

The aim of these actions of adenosine is to increase the oxygen supply of the affected organs and/or to reduce the metabolism of these organs in order to adjust the metabolism of the organ to the blood supply of the organ under ischaemic or hypoxic conditions.

The action of adenosine is mediated via specific receptors. To date, subtypes A1, A2a, A2b and A3 are known. The actions of these adenosine receptors are mediated intracellularly by the messenger cAMP. In the case of the binding of adenosine to the A2a or A2b receptors, the intracellular cAMP is increased via activation of the membrane-bound adenylate cyclase, whereas binding of adenosine to A1 or A3 receptors results in a decrease of the intracellular cAMP concentration via inhibition of adenylate cyclase.

According to the invention, "adenosine-receptor-selective ligands" are substances which bind selectively to one or more subtypes of the adenosine receptors, thus either mimicking the action of adenosine (adenosine agonists) or blocking its action (adenosine antagonists).

In the context of the present invention, adenosine receptor ligands are referred to as being "selective" if, firstly, they are clearly active on one or more adenosine receptor subtypes and, secondly, the activity that can be observed on one or more other adenosine receptor subtypes is considerably weaker (factors 10 or less), if present at all, where, with respect to the test methods for selectivity of action, reference is made to the test methods described in section A.II.

According to their receptor selectivity, adenosine-receptor-selective ligands can be divided into different categories, for example ligands which bind selectively to the A1 or A2 receptors of adenosine and in the case of the latter also, for example, those which bind selectively to the A2a or A2b receptors of adenosine. Also possible are adenosine receptor ligands which bind selectively to a plurality of subtypes of the adenosine receptors, for example ligands which bind selectively to the A1 and the A2, but not to the A3 receptors of adenosine.

The abovementioned receptor selectivity can be determined by the effect of the substances on cell lines which, after stable transfection with the corresponding cDNA, express the receptor subtypes in question (see the publication M. E. Olah, H. Ren, J. Ostrowski, K. A. Jacobson, G. L. Stiles, "Cloning, expression, and characterization of the unique bovine A1 adenosine receptor. Studies on the ligand binding site by site-directed mutagenesis." in *J. Biol. Chem.* 267 (1992) pages 10764–10770, the disclosure of which is hereby fully incorporated by way of reference).

The effect of the substances on such cell lines can be monitored by biochemical measurement of the intracellular messenger cAMP (see the publication K. N. Klotz, J. Hessling, J. Hegler, C. Owman, B. Kull, B. B. Fredholm, M. J. Lohse, "Comparative pharmacology of human adenosine receptor subtypes—characterization of stably transfected receptors in CHO cells" in *Naunyn Schmiedebergs Arch. Pharmacol.* 357 (1998) pages 1–9, the disclosure of which is hereby fully incorporated by way of reference).

In the case of A1 agonists (coupling preferably via $G_i$ proteins), a decrease of the intracellular cAMP concentration is observed (preferably after direct prestimulation of adenylate cyclase by forskolin), in the case of A1 antagonists an increase in the intracellular cAMP concentration is observed (preferably after prestimulation with adenosine or adenosine-like substances plus direct prestimulation of adenylate cyclase by forskolin). Correspondingly, A2a and A2b agonists (coupling preferably via $G_s$ proteins) lead to an increase and A2a and A2b antagonists to a decrease of the cAMP concentration in the cells. In the case of A2 receptors, a direct prestimulation of adenylate cyclase by forskolin is of no benefit.

The "adenosine-receptor-specific" ligands known from the prior art are mainly derivatives based on natural adenosine (S.-A. Poulsen, and R. J. Quinn, "Adenosine receptors: new opportunities for future drugs" in *Bioorganic and Medicinal Chemistry* 6 (1998) pages 619 to 641). However, most of the adenosine ligands known from the prior art have the disadvantage that their action is not really receptor-specific, that their activity is less than that of natural adenosine or that they have only very weak activity after oral administration. Thus they are mainly used only for experimental purposes.

In addition, WO 00/125210 discloses 2-thio-3,5-dicyano-4-aryl-6-aminopyridines of a structure similar to that of the compounds of the invention. However, the pharmacokinetical properties of the compounds described therein are less advantageous; in particular, they have poor bioavailability after oral administration.

It is now an object of the present invention to find or provide compounds which do not have the disadvantages of the prior art and/or have improved bioavailability.

Accordingly, the present invention relates to compounds of the formula (I)

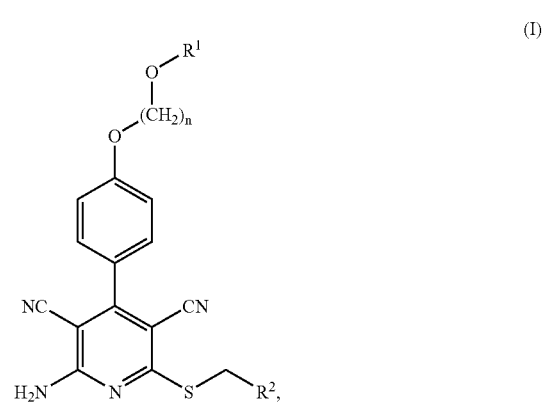

in which n represents a number 2, 3 or 4, $R^1$ represents hydrogen or $(C_1–C_4)$-alkyl and $R^2$ represents pyridyl or thiazolyl which for its part may be substituted by $(C_1–C_4)$-alkyl, halogen, amino, dimethylamino, acetylamino, guanidino, pyridylamino, thienyl, furyl, imidazolyl, pyridyl, morpholinyl, thiomorpholinyl, piperidinyl, piperazinyl, N-$(C_1–C_4)$-alkylpiperazinyl, pyrrolidinyl, oxazolyl, isoxazolyl, pyrimidinyl, pyrazinyl, optionally $(C_1–C_4)$-alkyl-substituted thiazolyl or phenyl which is optionally substituted up to three times by halogen $(C_1–C_4)$-alkyl or $(C_1–C_4)$-alkoxy, and their salts, hydrates, hydrates of the salts and solvates.

Depending on the substitution pattern, the compounds of the formula (I) can exist in stereoisomeric forms which are either like image and mirror image (enantiomers) or not like image and mirror image (diastereomers). The invention relates both to the enantiomers or diastereomers and to their respective mixtures. The racemic forms, like the diastereomers, can be separated in a known manner into the stereoisomerically uniform components. Likewise, the present invention also relates to the other tautomers of the compounds of the formula (I) and their salts.

Salts of the compounds of the formula (I) can be physiologically acceptable salts of the compounds according to the invention with mineral acids, carboxylic acids, or sulphonic acids. Particular preference is given, for example, to salts with hydrochloric acid, hydrobromic acid, sulphuric acid, phosphoric acid, methanesulphonic acid, ethanesulphonic acid, toluenesulphonic acid, benzenesulfonic acid, naphthalenedisulphonic acid, trifluoroacetic acid, acetic acid, propionic acid, lactic acid, tartaric acid, citric acid, fumaric acid, maleic acid or benzoic acid.

Salts which may be mentioned include salts with customary bases, such as, for example, alkali metal salts (for example sodium salts or potassium salts), alkaline earth metal salts (for example calcium salts or magnesium salts) or ammonium salts, derived from ammonia or organic amines, such as, for examples, diethylamine, triethylamine, ethyldiisopropylamine, procaine, dibenzylamine, N-methylmorpholine, dihydroabietylamine, 1-ephenamine or methylpiperidine.

According to the invention, hydrates or solvates are those forms of the compounds of the formula (I) which, in solid or liquid state, form, by hydration with water or coordination with solvent molecules, a molecule compound or a complex. Examples of hydrates are sesquihydrates, monohydrates, dihydrates or trihydrates. Likewise, the hydrates or solvates of salts of the compounds according to the invention are also suitable.

Moreover, the invention also includes prodrugs of the compounds according to the invention. According to the invention, prodrugs are forms of compounds of the formula (I) which for their part may be biologically active or inactive, but which can be converted under physiological conditions (for example metabolically or solvolytically) into the corresponding biologically active form.

In the context of the present invention, the substituents have, unless defined otherwise, the following meanings:

Halogen generally represents fluorine, chlorine, bromine or iodine. Preference is given to fluorine, chlorine or bromine. Very particularly preferred are fluorine or chlorine.

$(C_1–C_4)$-Alkyl generally represents a straight-chain or branched alkyl radical having 1 to 4 carbon atoms. Examples which may be mentioned are: methyl, ethyl, n-propyl, isopropyl, n-butyl, sec-butyl, isobutyl and tert-butyl.

$(C_1–C_4)$-Alkoxy generally represents a straight-chain or branched alkoxy radical having 1 to 4 carbon atoms. Examples which may be mentioned are: methoxy, ethoxy, n-propoxy, isopropoxy, n-butoxy, sec-butoxy, isobutoxy and tert-butoxy.

Preference is given to compounds of the formula (I)

in which n represents the number 2, $R^1$ represents hydrogen, methyl or ethyl, and $R^2$ represents pyridyl or thiazolyl which for its part may be substituted by methyl, ethyl, fluorine, chlorine, amino, dimethylamino, acetylamino, guanidino, 2-pyridylamino, 4-pyridylamino, thienyl, pyridyl, morpholinyl, piperidinyl, optionally methyl-substituted thiazolyl or phenyl which is optionally substituted up to three times by chlorine or methoxy, and their salts, hydrates, hydrates of the salts and solvates.

Particular preference is given to compounds of the formula (I) in which $R^1$ is hydrogen or methyl.

Particular preference is also given to compounds of the formula (I) in which n represents the number 2, $R^1$ represents hydrogen or methyl and $R^2$ represents pyridyl or thiazolyl which for its part may be substituted by methyl, chlorine, amino, dimethylamino, acetylamino, guanidino, 2-pyridyl-amino, 4-pyridylamino, thienyl, pyridyl, morpholinyl, 2-methylthiazol-5-yl, phenyl, 4-chlorophenyl or 3,4,5-trimethoxyphenyl, and their salts, hydrates, hydrates of the salts and solvates.

Very particular preference is given to the compound from Example 6 of the following structure

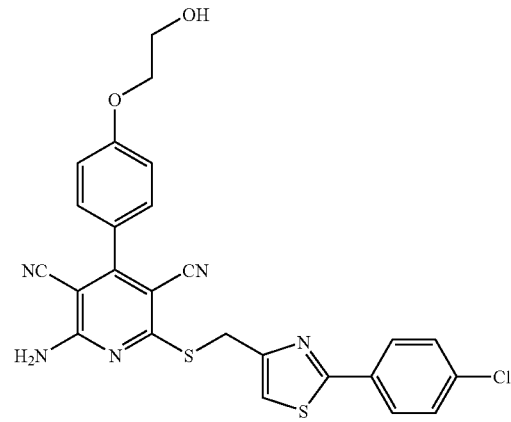

and their salts, hydrates, hydrates of the salts and solvates.

The present invention also provides a process for preparing compounds of the formula (I), characterized in that compounds of the formula (II)

(II)

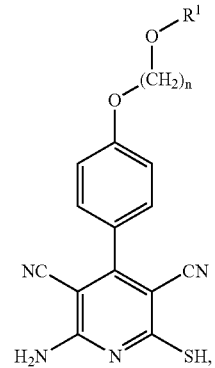

in which n and $R^1$ are as defined above, are reacted with compounds of the formula (III)

$$R^2—CH_2-X \quad (III),$$

in which $R^2$ is as defined above and X represents a suitable leaving group, by way of example and by way of preference halogen, in particular chlorine, bromine or iodine, or represents mesylate, tosylate, triflate or 1-imidazolyl, if appropriate in the presence of a base.

The process described above can be illustrated in an exemplary manner by the formula scheme below:

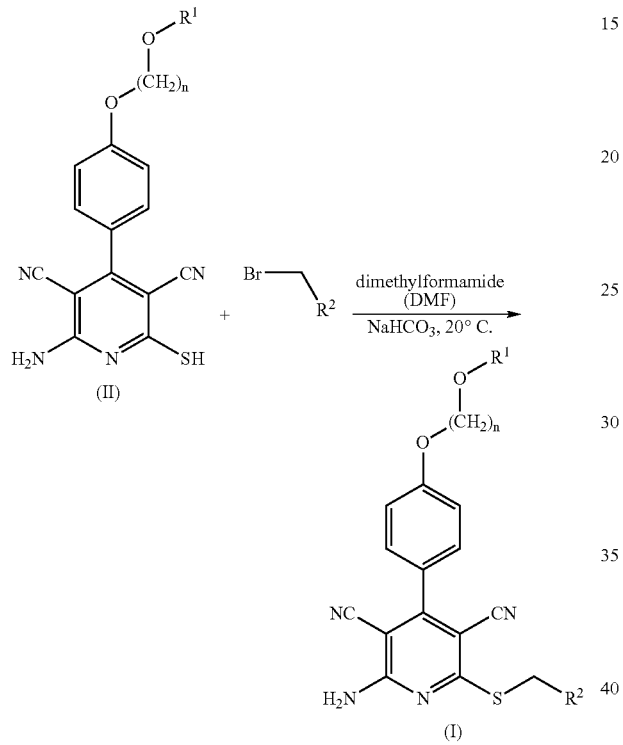

Suitable solvents for the process according to the invention are all organic solvents which are inert under the reaction conditions. These include alcohols, such as methanol, ethanol and isopropanol, ketones, such as acetone and methyl ethyl ketone, acyclic and cyclic ethers, such as diethyl ether and tetrahydrofuran, esters, such as ethyl acetate or butyl acetate, hydrocarbons, such as benzene, xylene, toluene, hexane or cyclohexane, chlorinated hydrocarbons, such as dichloromethane, chlorobenzene or dichloroethane, or other solvents, such as dimethylformamide, acetonitrile, pyridine or dimethyl sulphoxide (DMSO). Water, too, is a suitable solvent. Preference is given to dimethylformamide. It is also possible to use mixtures of the solvents mentioned above.

Suitable bases are the customary inorganic or organic bases. These preferably include alkali metal hydroxides, such as, for example, sodium hydroxide or potassium hydroxide, or alkali metal carbonates, such as sodium carbonate or potassium carbonate, or alkali metal bicarbonates, such as sodium bicarbonate or potassium bicarbonate, or alkali metal alkoxides, such as sodium methoxide or potassium methoxide, sodium ethoxide or potassium ethoxide or potassium tert-butoxide, or amides, such as sodium amide, lithium bis(trimethylsilyl)amide or lithium diisopropylamide, or organometallic compounds, such as butyllithium or phenyllithium, or 1,8-diazabicylco[5,4,0]undec-7-ene (DBU) or 1,5-diazabicylo-[4.3.0]non-5-ene (DBN), or else amines, such as triethylamine and pyridine. Preference is given to the alkali metal carbonates and alkali metal bicarbonates.

Here, the base can be employed in an amount of from 1 to 10 mol, preferably from 1 to 5 mol, in particular from 1 to 4 mol, based on 1 mol of the compounds of the formula (II).

The reaction generally takes place in a temperature range of from −78° C. to +140° C., preferably in the range from −78° C. to +40° C., in particular at room temperature.

The reaction can be carried out at atmospheric, elevated or reduced pressure (for example in the range from 0.5 to 5 bar). In general, the reaction is carried out at atmospheric pressure.

The compounds of the formula (II) are known per se to the person skilled in the art or can be prepared by customary methods known from the literature, for example by reacting the corresponding benzaldehydes with cyanothioacetamide. Reference may be made in particular to the following publications, the respective content of which is expressly incorporated herein by way of reference:

Dyachenko et al., Russian Journal of Chemistry, Vol. 33, No. 7, 1997, pages 1014 to 1017 and Vol. 34, No. 4, 1998, pages 557 to 563, Dyachenko et al., Chemistry of Heterocyclic Compounds, Vol. 34, No. 2, 1998, pages 188 to 194;

Qintela et al., European Journal of Medicinal Chemistry, Vol. 33, 1998, pages 887 to 897;

Kandeel et al., Zeitschift für Naturforschung 42b, 107 to 111 (1987).

Thus, for example, it is also possible to prepare compounds of the formula (II) from compounds of the formula (IV) by reaction with an alkali metal sulphide. This preparation method can be illustrated, by way of example, by the following formula scheme:

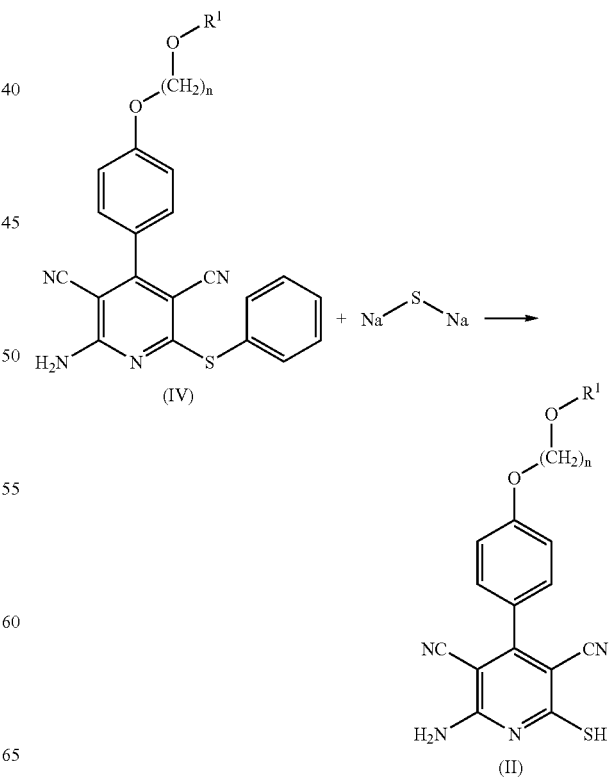

The alkali metal sulphide used is preferably sodium sulphide in an amount of from 1 to 10 mol, preferably from 1 to 5 mol, in particular from 1 to 4 mol, based on 1 mol of the compounds of the formula (IV).

Suitable solvents are all organic solvents which are inert under the reaction conditions. These include, for example, N,N-dimethylformamide, N-methylpyrrolidinone, pyridine and acetonitrile. Preference is given to N,N-dimethylformamide. It is also possible to use mixtures of the solvents mentioned above.

The reaction is generally carried out in a temperature range of from +20° C. to +140° C., preferably in the range from +20° C. to +120° C., in particular at from +60° C. to +100° C.

The reaction can be carried out in atmospheric, elevated or reduced pressure (for example in the range from 0.5 to 5 bar). In general, the reaction is carried out at atmospheric pressure.

The compounds of the formula (III) are either commercially available or known to the person skilled in the art or can be prepared by customary methods.

The compounds of the formula (IV) are either commercially available or known to the person skilled in the art or can be prepared by customary methods. Reference may be made, in particular, to the following publications, the respective content of which is expressly incorporated herein by way of reference.

Kambe et al., Synthesis, 531 to 533 (1981);
Elnagdi et al., Z. Naturforsch. 47b, 572 to 578 (1991).

The pharmaceutical activity of the compounds of the formula (I) can be explained by their action as selective ligands or adenosine A1 receptors. Here, they act as A1 agonists.

Surprisingly, the compounds of the formula (I) have an unforeseeable useful pharmacological activity spectrum and are therefore suitable in particular for the prophylaxis and/or treatment of disorders.

Compared to the prior art, the compounds of the formula (I) according to the invention have improved pharmacokinetic properties, in particular better bioavailability after oral administration.

The compounds of the formula (I), alone or in combination with one or more other active compounds, are suitable for the prophylaxis and/or treatment of various disorders, i.e. in particular, for example, disorders of the cardiovascular system (cardiovascular disorders). Active compounds suitable for combinations are in particular active compounds for treating coronary heart disease, such as, for example, in particular nitrates, beta blockers, calcium antagonists or diuretics.

In the context of the present invention, cardiovascular disorders are to be understood as meaning, in particular, for example the following disorders: coronary restenosis, such as, for example, restenosis after balloon dilation of peripheral blood vessels, tachycardia, arrhythmias; peripheral and cardiovascular disorders, stable and unstable angina pectoris, atrial and ventricular fibrillation.

The compounds of the formula (I) are furthermore also particularly suitable for example for reducing the size of myocardial area affected by an infarct.

The compounds of the formula (I) are furthermore particularly suitable, for example, for the prophylaxis and/or treatment of thromboembolic disorders and ischaemias, such as myocardial infarction, stroke and transitory ischaemic attacks.

Further areas of indication for which the compounds of the formula (I) are particularly suitable are, for example, the prophylaxis and/or treatment of disorders of the urogenital region, such as, for example, irritable bladder, erectile dysfunction and female sexual dysfunction, and additionally also the prophylaxis and/or treatment of inflammatory disorders, such as, for example, asthma and inflammable dermatoses, of neuroinflammatory disorders of the central nervous system, such as, for example, conditions after cerebral infarction, Alzheimer's disease, furthermore also neurodegenerative disorders, as well as pain, and cancer.

A further particular area of indication is, for example, the prophylaxis and/or treatment of disorders of the respiratory tract, such as, for example, asthma, chronic bronchitis, pulmonary emphysema, bronchiectases, cystic fibrosis (mucoviscidosis) and pulmonary hypertension.

Finally, the compounds of the formula (I) are in particular also suitable, for example, for the prophylaxis and/or treatment of diabetes, in particular diabetes mellitus.

The present invention also relates to the use of the compounds of the formula (I) for preparing medicaments for the prophylaxis and/or treatment of the clinical pictures mentioned above.

The present invention furthermore relates to a method for the prophylaxis and/or treatment of the clinical pictures mentioned above using the compounds of the formula (I).

The subject-matter of the present invention furthermore includes medicaments comprising at least one compounds of the formula (I), preferably together with one or more pharmacologically acceptable auxiliaries or carriers, and their use for the purposes mentioned above.

Suitable for administering the compounds of the formula (I) are all customary administration forms, i.e. oral, parenteral, inhalative, nasal, sublingual, rectal, local, such as, for example, in the case of implants or stents, or external, such as, for example, transdermal. In the case of parenteral administration, particular mention may be made of intravenous, intramuscular and subcutaneous administration, for example as a subcutaneous depot. Preference is given to oral or parenteral administration. Particular preference is given to oral administration.

Here, the active compounds can be administered on their own or in the form of preparations. Suitable preparations for oral administration are inter alia tablets, capsules, pellets, sugar-coated tablets, pills, granules, solid and liquid aerosols, syrups, emulsions, suspensions and solutions. Here, the active compound has to be present in such a quantity that a therapeutic effect is obtained. In general, the active compound can be present in a concentration of from 0.1 to 100% by weight, in particular from 0.5 to 90% by weight, preferably from 5 to 80% by weight. In particular, the concentration of the active compound should be from 0.5 to 90% by weight, i.e. the active compound should be present in quantities sufficient to achieve the dosage range mentioned.

To this end, the active compounds can be converted in a manner known per se to the customary preparations. This is achieved using inert nontoxic pharmaceutically suitable carriers, auxiliaries, solvents, vehicles, emulsifiers and/or dispersants.

Auxiliaries which may be mentioned are, for example: water, nontoxic organic solvents, such as, for example, paraffins, vegetable oils (for example sesame oil), alcohols (for example ethanol, glycerol), glycols (for example polyethylene glycol), solid carriers, such as natural or synthetic ground minerals (for example talc or silicates), sugars (for example lactose), emulsifiers, dispersants (for example polyvinylpyrrolidone) and glidants (for example magnesium sulphate).

In the case of oral administration, tablets may, of course, also contain additives such as sodium citrate, together with adjuvants such as starch, gelatin and the like. Aqueous preparations for oral administration may furthermore be admixed with flavour enhancers or colorants.

In general, it has been found to be advantageous to administer, in the case of parenteral administration, quantities of from about 0.1 to about 10 000 μg/kg, preferably from about 1 to about 1000 μg/kg, in particular from about 1 μg/kg to about 100 μg/kg, of body weight, to obtain effective results. In the case of oral administration, the quantity is from about 0.05 to about 5 mg/kg, preferably from about 0.1 to about 5 mg/kg, in particular from about 0.1 to about 1 mg/kg, of body weight.

In spite of this, it may still be required, depending on body weight, administration route, individual response to the active compound, the type of preparation and the time or interval at which administration takes place, to deviate from the quantities mentioned.

The present invention is illustrated by the following non-limiting preferred examples, which do not restrict the invention in any way.

In the examples below, the percentages are, unless indicated otherwise, in each case based on weight; parts are parts by weight.

A. Assessing the Physiological Activity

I. Detecting the Cardiovascular Effect

After the thorax has been opened, the heart is rapidly removed from anaesthetized rats and introduced into a conventional Langerdorff apparatus. The coronary arteries are perfused at constant volume (10 ml/min), and the resulting perfusion pressure is recorded by way of an appropriate pressure sensor. In this set-up, a decrease in the perfusion pressure corresponds to a relaxation of the coronary arteries. At the same time, the pressure which the heart develops during each contraction is measured by way of a balloon, which has been introduced into the left ventricle, and a second pressure sensor. The frequency of the heart, which is beating in isolation, is calculated from the number of contractions per time unit.

In this experimental set-up, the following values were obtained for the reduction in heart rate (the stated percentage refers to the reduction of the heart rate in per cent at the concentration in question):

| Compound of Example | Reduction of the heart rate in percent at a concentration of | |
| --- | --- | --- |
| | $10^{-7}$ g/ml | $10^{-6}$ g/ml |
| 1 | 15.0% | 17.5% |
| 6 | 15.5% | 20.0% |

II. Determining the Adenosine A1, A2a, A2b and A3 Agonism a) Determining the Adenosine Agonism Indirectly by Way of Gene Expression Cells of the CHO (Chinese Hamster Ovary) permanent cell line are transfected stably with the cDNA for the adenosine receptor subtypes A1, A2a and A2b. The adenosine A1 receptors are coupled to the adenylate cyclase by way of Gi proteins, while the adenosine A2a and A2b receptors are coupled by way of Gs proteins. In correspondence with this, the formation of cAMP in the cell is inhibited or stimulated, respectively. After that, expression of the luciferase is modulated by way of a cAMP-dependent promoter. The luciferase test is optimized, with the aim of high sensitivity and reproducibility, low variance and good suitability for implementation on a robot system, by varying several test parameters, such as cell density, duration of the growth phase and the test incubation, forskolin concentration and medium composition. The following test protocol is used for pharmacologically characterizing cells and for the robot-assisted substance test screening.

The stock cultures are grown, at 37° C. and under 5% $CO_2$, in DMEM/F12 medium containing 10% FCS (foetal calf serum) and in each case split 1:10 after 2–3 days. The test cultures are seeded in 384-well plates at the rate of from 1 000 to 3 000 cells per well and grown at 37° C. for approx. 48 hours. The medium is then replaced with a physiological sodium chloride solution (130 mM sodium chloride, 5 mM potassium chloride, 2 mM calcium chloride, 20 mM HEPES, 1 mM magnesium chloride $6H_2O$, 5 mM $NaHCO_3$, pH 7.4). The substances, which are dissolved in DMSO, are diluted 1:10 three times with this physiological sodium chloride solution and pipetted into the test cultures (maximum final concentration of DMSO in the test mixture: 0.5%). In this way, final substance concentrations of, for example, from 5 μM to 5 nM are obtained. 10 minutes later, forskolin is added to the A1 cells and all the cultures are subsequently incubated at 37° C. for four hours. After that, 35 μl of a solution which is composed of 50% lysis reagent (30 mM disodium hydrogenphosphate, 10% glycerol, 3% TritonX100, 25 mM TrisHCl, 2 mM dithiothreitol (DTT), pH 7.8) and 50% luciferase substrate solution (2.5 mM ATP, 0.5 mM luciferin, 0.1 mM coenzyme A, 10 mM tricine, 1.35 mM magnesium sulphate, 15 mM DTT, pH 7.8) are added to the test cultures, the plates are shaken for approx. 1 minute and the luciferase activity is measured using a camera system. The adenosine-analogous compound NECA (5-N-ethylcarboxamido-adenosine), which binds to all adenosine receptor subtypes with high affinity and possesses an agonistic effect, is used in these experiments as the reference compound (Klotz, K. N., Hessling, J., Hegler, J., Owman, C., Kull, B., Fredholm, B. B., Lohse, M. J., Comparative pharmacology of human adenosine receptor subtypes—characterization of stably transfected receptors in CHO cells, Naunyn Schmiedebergs Arch Pharmacol, 357 (1998), 1–9).

The following Table 1 gives the values which were obtained for the stimulation of different adenosine receptor subtypes by different concentrations of the compound from Examples 1 and 6.

TABLE 1

Stimulation of adenosine receptors by different concentrations of the compound from Examples 1 and 6

| Receptor subtype | Example 1 | | | Example 6 | | |
| --- | --- | --- | --- | --- | --- | --- |
| | 10 nmol | 1 nmol | 0.3 nmol | 10 nmol | 1 nmol | 0.3 nmol |
| A1 | 4% | 11% | 56% | 7% | 25% | 45% |
| A2a | −2% | 2% | −1% | 2% | 4% | 0% |
| A2b | 8% | 6% | 2% | 29% | 3% | 0 |

The table gives the % values of the corresponding reference stimulus. The measured values for the A2a and A2b receptors are values in per cent of the maximum stimulation achieved by NECA; the measured values for the A1 receptor are values in per cent following direct prestimulation of the adenylate cyclase with 1 μmolar forskolin (corresponds to the 100% value). A1 agonists accordingly exhibit a decrease in the activity of the luciferase (measured value less than 100%).

b) Determining the Adenosine Agonism Directly by Way of Detecting cAMP

Cells of the CHO (Chinese Hamster Ovary) permanent cell line are transfected stably with the cDNA for the adenosine receptor subtypes A1, A2a, A2b and A3. The binding of the substances to the A2a or A2b receptor subtypes is determined by measuring the intracellular cAMP content in these cells using a conventional radioimmunological assay (cAMP RIA, IBL GmbH, Hamburg, Germany).

When the substances act as agonists, the binding of the substances is expressed as an increase in the intracellular content of cAMP. The adenosine-analogous compound NECA (5-N-ethylcarboxamido-adenosine), which binds all adenosine receptor subtypes with high affinity but not selectively and possesses an agonistic effect, is used as the reference compound in these experiments (Klotz, K. N., Hessling, J., Hegler, J., Owman, C., Kull, B., Fredholm, B. B., Lohse, M. J., Comparative pharmacology of human adenosine receptor subtypes—characterization of stably transfected receptors in CHO cells, Naunyn Schmeidebergs Arch Phamacol, 357 (1998), 1–9.

The adenosine receptors A1 and A3 are coupled to a $G_i$ protein, i.e. stimulation of these receptors leads to inhibition of the adenylate cyclase and consequently to a lowering of the intracellular cAMP level. In order to identify A1/A3 receptor agonists, the adenylate cyclase is stimulated with forskolin. However, an additional stimulation of the A1/A3 receptors inhibits the adenylate cyclase, which means that A1/A3 receptor agonists can be detected by a comparatively low content of cAMP in the cell.

In order to detect an antagonistic effect on adenosine receptors, the recombinant cells which are transfected with the corresponding receptor are prestimulated with NECA and the effect of the substances on reducing the intracellular content of cAMP occasioned by this prestimulation is investigated. XAC (xanthine amine congener), which binds to all adenosine receptor subtypes with high affinity and possesses an antagonistic effect, is used as the reference compound in these experiments (Müller, C. E., Stein, B., Adenosine receptor antagonists: structures and potential therapeutic applications, Current Pharmaceutical Design, 2 (1996) 501–530.

III. Pharmacokinetic Investigations

Pharmacokinetic data were determined after administering various substances i.v. or p.o. as solutions to mice, rats and dogs. For this, blood samples were collected up to 24 hours after administration. The concentrations of the unaltered substance were determined by bioanalytical methods (HPLC or HPLC-MS) in the plasma samples which were obtained from the blood samples. Pharmacokinetic parameters were subsequently ascertained from the plasma concentration time courses which had been obtained in this way. The following Table 2 gives the bioavailability in the different species.

TABLE 2

Bioavailabilities following oral administration

| | Mouse | Rat | Dog |
|---|---|---|---|
| Example 22 in WO 00/125210 | not possible to determine* (at 3 mg/kg p.o.) | not possible to determine* (at 10 mg/kg p.o.) | 1.47% (at 1 mg/kg p.o.) |
| Compound from Example 1 | 31.5% (at 1 mg/kg p.o.) | 5.0% (at 3 mg/kg p.o.) | 32.6% (at 3 mg/kg p.o.) |

TABLE 2-continued

Bioavailabilities following oral administration

| | Mouse | Rat | Dog |
|---|---|---|---|
| Compound from Example 6 | 41.3% (at 3 mg/kg p.o.) | 42.3% (at 3 mg/kg p.o.) | 28.5% (at 1 mg/kg p.o.) |

*Plasma levels at all measurement time points were below the determination limit (<1 µg/l)

B. Working Examples

| Abbreviations used: | |
|---|---|
| DBU | 1,8-diazabicyclo[5.4.0]undec-7-ene |
| DMF | dimethylformamide |
| ESI | electrospray ionization (for MS) |
| HEPES | 2-[4-(2-hydroxyethyl)piperazino]ethanesulphonic acid |
| HPLC | high pressure, high performance liquid chromatography |
| b.p. | boiling point |
| MS | mass spectroscopy |
| NMR | nuclear magnetic resonance spectroscopy |
| p.a. | pro analysi |
| RT | room temperature |
| Tris | 2-amino-2-(hydroxymethyl)-1,3-propanediol |

PREPARATION EXAMPLES

Example 1

2-Amino-4-[4-(2-methoxyethoxy)phenyl]-6-[(3-pyridinylmethyl)sulphanyl]pyridine-3,5-dicarbonitrile Step 1:

4-(2-Methoxyethoxy)benzaldehyde

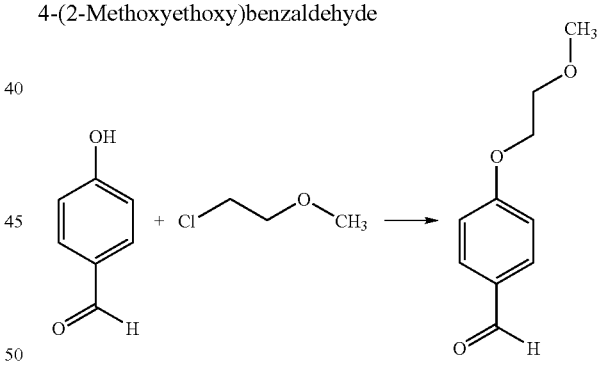

146.5 g (1.2 mol) of 4-hydroxybenzaldehyde are dissolved in DMF, and 20 g (0.12 mol) of potassium iodide, 134.6 g (1.2 mol) of potassium tert-butoxide and 170.2 g (1.8 mol) of 2-chloroethyl methyl ether are added. The reaction mixture is stirred at 80° C. for 16 h. For work-up, the reaction mixture is concentrated under reduced pressure. The residue is taken up in 1 l of ethyl acetate and extracted with 0.5 l of 1N aqueous sodium hydroxide solution. The ethyl acetate phase is dried using magnesium sulphate and concentrated under reduced pressure. The residue obtained after concentration is distilled under high vacuum (b.p.=100° C. at 0.45 mbar). This gives 184.2 g (85% of theory) of product.

MS (ESIpos): m/z=181 (M+H)$^{+1}$H-NMR (300 MHz, CDCl$_3$): δ=3.5 (s, 3H); 3.8 (tr, 2H); 4.2 (tr, 2H); 7.0 (d, 2H); 7.8 (d, 1H); 9.9 (s, 1H).

Step 2:

2-Amino-4-[4-(2-methoxyethoxy)phenyl]-6-sulphanylpyridine-3,5-dicarbonitrile

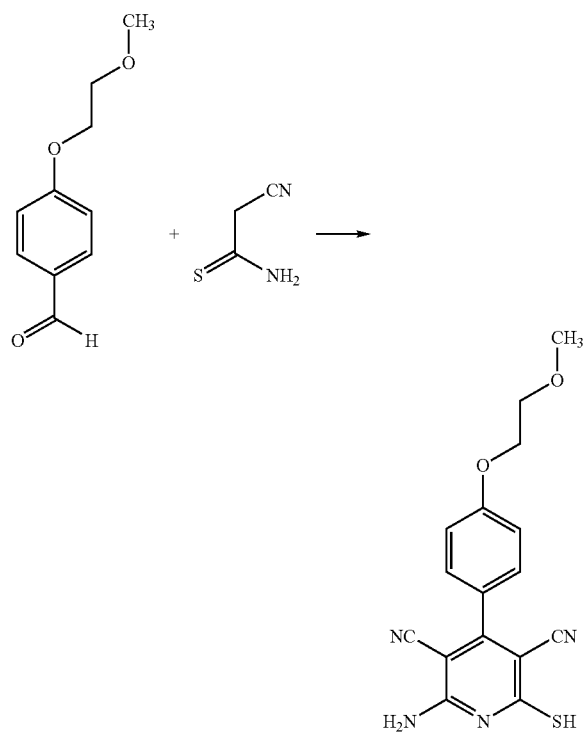

18 g (100 mmol) of 4-(2-methoxyethoxy)benzaldehyde, 10 g (200 mmol) of cyanothioacetamide and 20.2 g (200 mmol) of N-methylmorpholine in 100 ml of ethanol are heated under reflux for 3 h. After cooling, the precipitated crystals are filtered off with suction, washed with a little ethanol and dried under reduced pressure. This gives 12 g (31% of theory) of product which contains 0.5 mol equivalent of N-methylmorpholine.

MS (ESIpos): m/z=327 (M+H)$^{+1}$H-NMR (300 MHz, DMSO-d$_6$): δ=2.8 (tr, 4H, N-methylmorpholine signal); 3.3 (s, 3H); 3.7 (m, 2H+4H N-methylmorpholine signal); 4.2 (tr, 2H); 7.1 (d, 2H); 7.4 (d, 2H); 7.6 (s, broad, 2H).

Step 3:

2-Amino-4-[4-(2-methoxyethoxy)phenyl]-6-[(3-pyridinylmethyl)sulphanyl]pyridine-3,5-dicarbonitrile

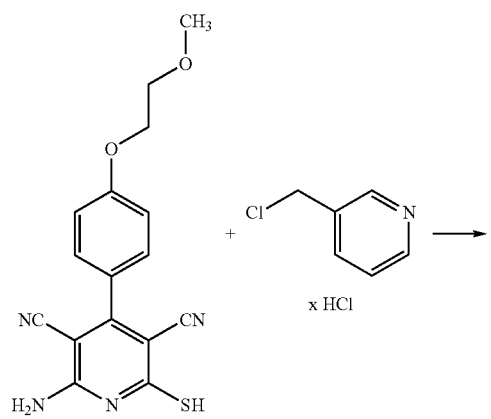

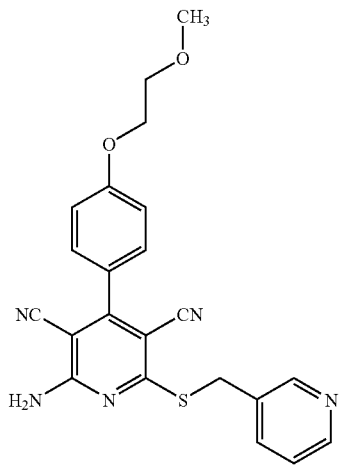

4.28 g (11.36 mmol; the starting material contained 0.5 mol equivalent of N-methylmorpholine; accordingly, the purity was 86.6%) of 2-amino-4-[4-(2-methoxyethoxy)phenyl]-6-sulphanylpyridine-3,5-carbonitrile are dissolved in 40 ml of DMF p.a. 3.34 g (39.75 mmol) of sodium bicarbonate and 2.48 g (15.1 mmol) of 3-picolyl chloride hydrochloride are then added. The suspension is stirred at RT overnight, 40 ml of ethanol are added and the mixture is then heated to about 40° C. 19 ml of water are then added dropwise. The precipitate is filtered off with suction and dried under reduced pressure. This gives 3.70 g (78% of theory) of product.

MS (ESIpos): m/z=418 (M+H)$^{+1}$H-NMR (300 MHz, DMSO-d$_6$): δ=3.3 (s, 3H); 3.7 (tr, 2H); 4.2 (tr, 2H); 4.5 (s, 2H); 7.1 (d, 2H); 7.35 (dd, 1H); 7.45 (d, 2H); 7.9 (d tr, 1H); 8.1 (s, broad, 2H); 8.45 (dd, 1H); 8.75 (d, 1H).

Example 2

2-Amino-6-[(2-chloro-1,3-thiazol-4-yl)methylsulphanyl]-[4-2-methoxyethoxy)-phenyl]pyridine-3,5dicarbonitrile

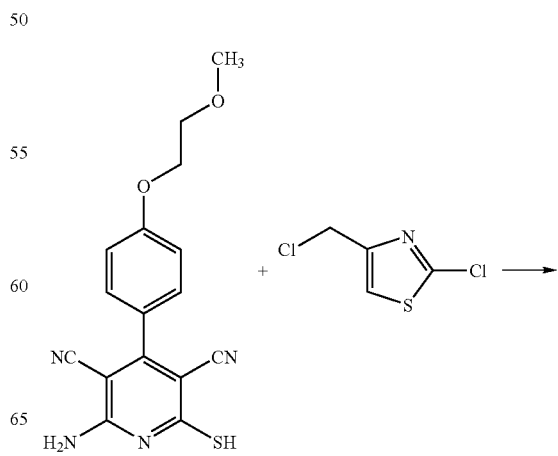

-continued

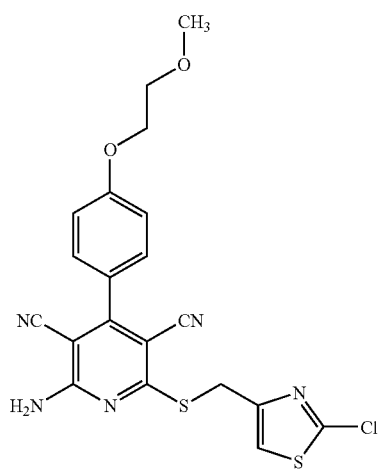

100 mg (0.31 mmol) of 2-amino-4-[4-(2-methoxyethoxy) phenyl]-6-sulphanyl-pyridine-3,5-dicarbonitrile are dissolved in 1 ml of DMF. 103 mg (1.23 mmol) of sodium bicarbonate and 77.2 mg (0.46 mmol) of 4-chloromethyl-2-chloro-1,3-thiazole are then added. The suspension is shaken at RT overnight, and water is added. The precipitate is filtered off with suction, washed with ethanol and diethyl ether and dried at 40° C. under reduced pressure. This gives 123 mg (88% of theory) of product.

MS (ESIpos): m/z=458 (M+H)$^{+1}$H=NMR (300 MHz, DMSO-d$_6$): δ=3.3 (s, 3H); 3.7 (tr, 2H); 4.2 (tr, 2H); 4.5 (s, 2H); 7.1 (d, 2H); 7.45 (d, 2H); 7.8 (s, 1H); 8.05 (s, broad, 2H).

-continued

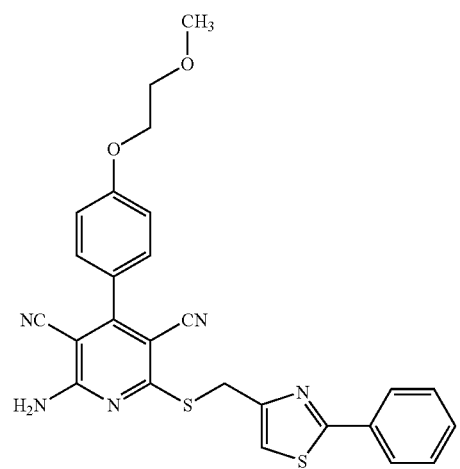

100 mg (0.31 mmol) of 2-amino-4-[4-(2-methoxyethoxy) phenyl]-6-sulphanyl-pyridine-3,5-dicarbonitrile are dissolved in 1 ml of DMF. 103 mg (1.23 mmol) of sodium bicarbonate and 96.4 mg (0.46 mmol) of 4-chloromethyl-2-phenyl-1,3-thiazole are then added. The suspension is shaken at RT overnight, and water is added. The precipitate is filtered off with suction, washed with ethanol and diethyl ether and dried at 40° C. under reduced pressure. This gives 149 mg (97% theory) of product.

MS (ESIpos): m/z=500 (M+H)$^{30}$ $^1$H=NMR (300 Hz, DMSO-d$_6$): δ=3.3 (s, 3H); 3.7 (tr, 2H); 4.2 (tr, 2H); 4.5 (s, 2H); 7.1 (d, 2H); 7.5 (m, 5H); 7.8 (s, 1H); 7.9 (m, 2H); 8.05 (s, broad, 2H).

Example 3

2-Amino-4-[4-(2-methoxyethoxy)phenyl]-6-[(2-phenyl-1,3-thiazol-4-yl)methyl-sulphanyl]pyridine-3,5-dicarbonitrile

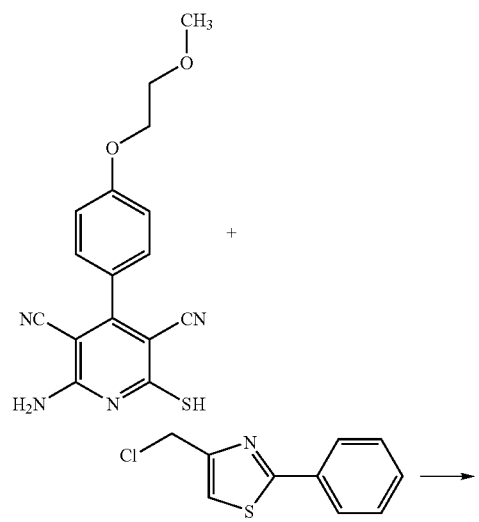

Example 4

2-Amino-4-[4-(2-methoxyethoxy)phenyl]-6-[(2-thiophen-2-yl)-1,3-thiazol-4-yl)-methylsulphanyl]-3,5-dicarbonitrile

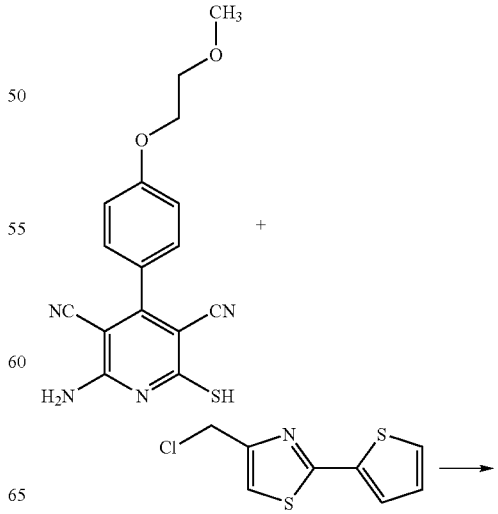

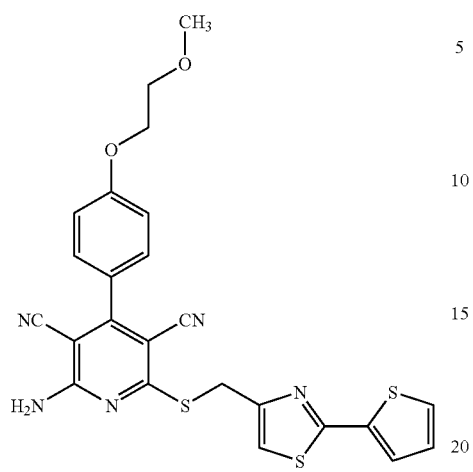

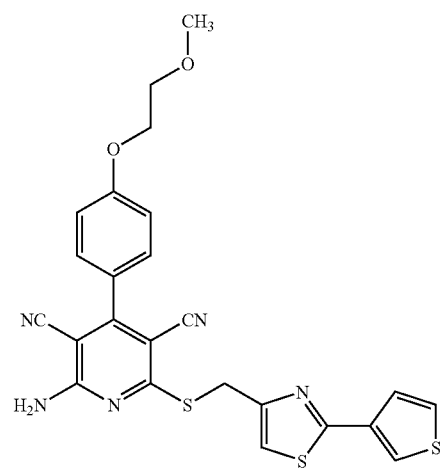

100 mg (0.31 mmol) of 2-amino-4-[4-(2-methoxyethoxy)phenyl]-6-sulphanyl-pyridine-3,5-dicarbonitrile are dissolved in 1 ml of DMF. 103 mg (1.23 mmol) of sodium bicarbonate and 96.4 mg (0.46 mmol) of 4-chloromethyl-2-(thiophen-2-yl)-1,3-thiazole are then added. The suspension is shaken at RT overnight, and water is added. The precipitate is filtered off with suction, washed with ethanol and diethyl ether and dried at 40° C. under reduced pressure. This gives 146 mg (84% of theory) of product.

MS (ESIpos): m/z=506 (M+H)$^{+1}$H=NMR (300 MHz, DMSO-$d_6$): δ=3.3 (s, 3H); 3.7 (tr, 2H); 4.2 (tr, 2H); 4.6 (s, 2H); 7.15 (m, 3H); 7.5 (d, 2H); 7.65 (d, 1H); 7.75 (d, 1H); 7.8 (s, 1H); 8.1 (s, broad, 2H).

100 mg (0.31 mmol) of 2-amino-4-[4-(2-methoxyethoxy)phenyl]-6-sulphanyl-pyridine-3,5-dicarbonitrile are dissolved in 1 ml of DMF. 103 mg (1.23 mmol) of sodium bicarbonate and 96.4 mg (0.46 mmol) of 4-chloromethyl-2-(thiophen-3-yl)-1,3-thiazole are then added. The suspension is shaken at RT overnight, and water is added. The precipitate is filtered off with suction, washed with ethanol and diethyl ether and dried at 40° C. under reduced pressure. This gives 141 mg (82% of theory) of product.

MS (ESIpos): m/z=506 (M+H)$^{+1}$H=NMR (300 MHz, DMSO-$d_6$): δ=3.3 (s, 3H); 3.7 (tr, 2H); 4.2 (tr, 2H); 4.6 (s, 2H); 7.15 (d, 2H); 7.5 (d, 2H); 7.55 (d, 1H); 7.7 (dd, 1H); 7.8 (s, 1H); 8.1 (s, broad, 2H); 8.15 (d, 1H).

Example 5

2-Amino-4-[4-(2-methoxyethoxy)phenyl]-6-[(2-(thiophen-3-yl)-1,3-thiazol-4-yl)-methylsulphanyl]pyridine-3,5-dicarbonitrile

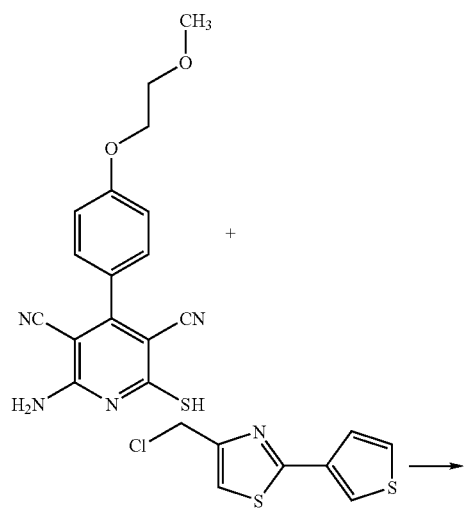

Example 6

2-Amino-6-({[2-(4-chlorophenyl)-1,3-thiazol-4-yl]methyl}sulphanyl)-4-[4-(2-hydroxyethoxy)phenyl]pyridine-3,5-dicarbonitrile Route 1

1st Step:

2-Amino-4-[4-(2-hydroxyethoxy)phenyl]-6-sulphanylpyridine-3,5-dicarbonitrile

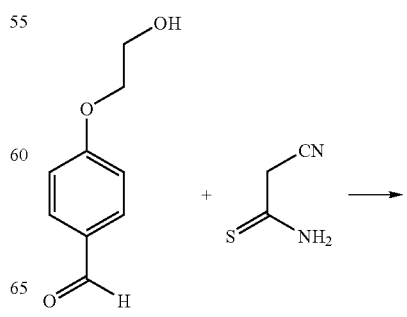

-continued

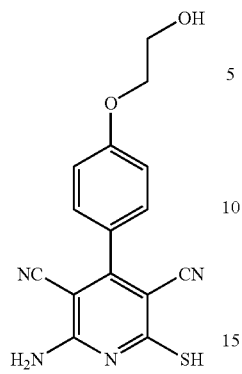

12.46 g (75 mmol) of 4-(2-hydroxyethoxy)benzaldehyde, 15.02 g (150 mmol) of cyanothioacetamide and 15.15 g (150 mmol) of N-methylmorpholine are initially charged in 75 ml of ethanol and heated under reflux for 3 h. After cooling, the reaction solution is concentrated under reduced pressure. The residue is dissolved in 1N aqueous sodium hydroxide solution and washed twice with ethyl acetate. The aqueous sodium hydroxide phase is acidified with 1N hydrochloric acid and the precipitated crystals are filtered off with suction and dried under reduced pressure at 45° C. This gives 12.05 g (51% of theory) of product.

MS (ESIpos): m/z=313 (M+H)$^+$, 330 (M+NH$_4$)$^+$ $^1$H=NMR (300 MHz, DMSO-d$_6$); δ=3.7 (t, 2H); 4.1 (t, 2H); 7.1 (d, 2H); 7.4 (d, 2H); 8.0 (br s, 2H).

2nd Step:

2-Amino-6-({[2-(4-chlorophenyl)-1,3-thiazol-4-yl]methyl}sulphanyl)-4-[4-(2-hydroxyethoxy)phenyl]pyridine-3,5-dicarbonitrile

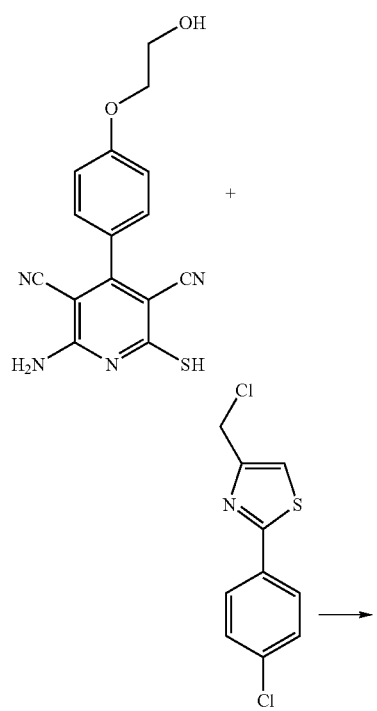

-continued

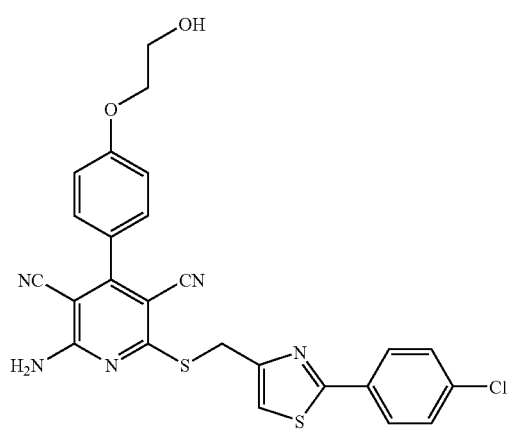

6.91 g (22.12 mmol) of 2-amino-4-[4-(2-hydroxyethoxy)phenyl]-6-sulphanyl-pyridine-3,5-dicarbonitrile are dissolved in 150 ml of DMF. 7.44 g (66.35 mmol) of 1,8-diazabicyclo[5.4.0]undec-7-ene and 10.8 g (44.24 mmol) of 4-chloromethyl-2-(4-chlorophenyl)-1,3-thiazole are then added. The suspension is stirred at RT overnight, 50 g of silica gel are added and the mixture is concentrated under reduced pressure. The substance mixture on the silica gel is purified by chromatography on silica gel (mobile phase: toluene to toluene/ethyl acetate, 1:1 mixture). This gives 5.5 g (47% of theory) of product.

MS (ESIpos): m/z=521 (M+H)$^{+1}$H=NMR (300 MHz, DMSO-d$_6$): δ=3.7 (dt, 2H); 4.1 (t, 2H); 4.6 (s, 2H); 4.9 (t, 1H); 7.1 (d, 2H); 7.4 (d, 2H); 7.5 (d, 2H); 7.9 (m, 3H); 8.1 (br s, 2H).

Route 2:

Alternatively, the product can also be prepared without isolating 2-amino-4-[4-(2-hydroxyethoxy)phenyl]-6-sulphanyl-3,5-pyridinedicarbonitrile by reacting 2-[4-(2-hydroxyethoxy)-benzylidene]malononitrile with 2-cyanothioacetamide and 4-chloromethyl-2-(4-chlorophenyl)-1,3-thiazole:

1st Step:

2-[4-(2-Hydroxyethoxy)-benzylidine]malononitrile

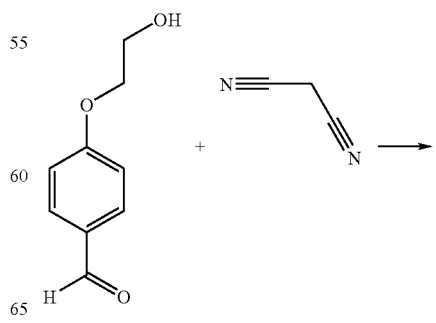

3rd Step:

2-Amino-6-({[2-(4-chlorophenyl)-1,3-thiazol-4-yl]methyl}sulphanyl)-4-[4-(2-hydroxyethoxy)phenyl]-3,5-pyridinedicarbonitrile

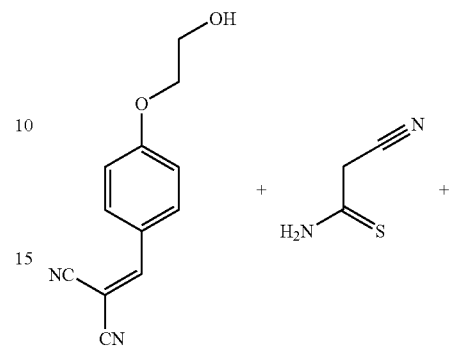

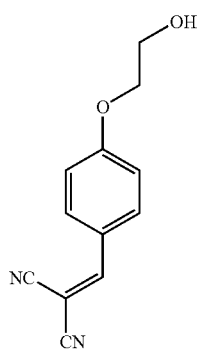

1000 g (5.85 mol) of 4-(2-hydroxyethoxy)benzaldehyde and 425 g (6.43 mol) of malonodinitrile are dissolved in 5000 ml of isopropyl alcohol and 5 g (0.059 mol) of piperidine are added. The mixture is heated to 80° C. for 16 hours and then cooled to 3° C. in order to isolate the product. The product is filtered off and washed with 400 ml of ice-cold isopropyl alcohol. Then it is dried in vacuo (40 mbar) at 50° C. for 45 hours.

Yield: 1206 g (94.6% of theory) of slightly yellow crystals
$^1$H (400 MHz, CDCl$_3$): 3.95–4.32 m (4 H), 6.95–7.15 (m, 2H), 7.61 (s, 1H), 7.85–7.95 (m, 1H).

2nd Step:

4-Chloromethyl-2-(4-chlorophenyl)-1,3-thiazole

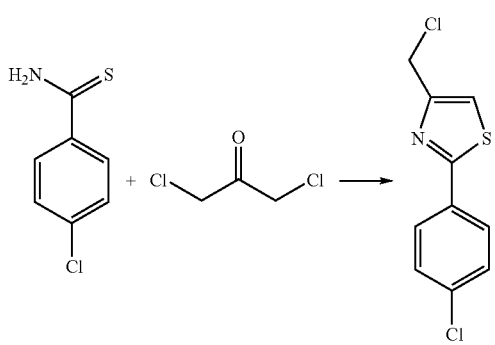

428.4 g (2.0 mol) of 2-[4-(2-hydroxyethoxy)-benzylidene]malononitrile, 108.4 g (1.05 mol) of 2-cyanothioacetamide and 244.1 g (1.0 mol) of 4-chloromethyl-2-(4-chlorophenyl)-1,3-thiazole are suspended in 3.4 liters of methanol and 556.1 g (3.0 mol) of tributylamine are added over a period of 60 minutes. The mixture is subsequently stirred for 20 hours at room temperature and the product is filtered off. After drying in vacuo, the crude product (360.8 g, crude yield: 70% of theory) is suspended in 3 liters of dichloromethane and stirred for 2 hours at 35° C. The product is filtered off and dried in a high vacuum. The crystals, which are now white, can be purified further by recrystallization from tetrahydrofuran/water (1:1).

Yield: 353.5 g (68% of theory) of white crystals MS(EI): m/z=520.00

Example 7

2-Amino-4-[4-(2-methoxyethoxy)phenyl]-6-[(2-pyridinylmethyl)sulphanyl]pyridine-3,5-dicarbonitrile

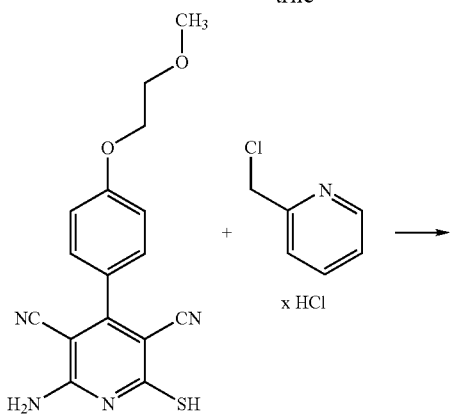

171.65 g (1.0 mol) of 4-chlorothiobenzamide are dissolved in 550 ml of isopropyl alcohol and 133.3 g (1.05 mol) of 1,3-dichloroacetone are added at a temperature of a maximum of 30° C. over a period of 3hours. The mixture is subsequently stirred at 40° C. for 5.5 hours and at 20° C. for 10 hours. In order to complete the reaction the mixture is then heated to 55° C. for 7.5 hours. The product is isolated by cooling to 10° C. and adding 950 ml of water. The pH value is adjusted to 4 to 5 using sodium hydroxide solution and the product is filtered off with suction.

Yield: 220.9 g (91% of theory) of white to slightly yellow crystals. $^1$H (400 MHz, CDCl$_3$): 4.90 (s, 2H, CH$_2$), 7.5–7.55 (m, 2H), 7.85 (s, 1H, thiazole), 7.9–7.95 (m, 2H)

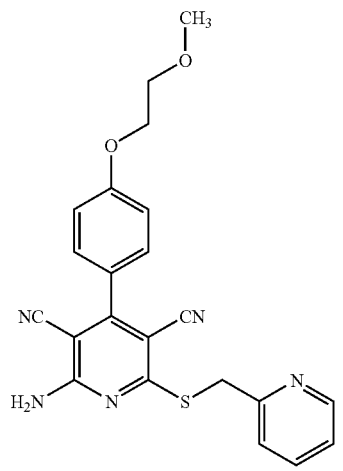

100 mg (0.31 mmol) of 2-amino-4-[4-(2-methoxyethoxy) phenyl]-6-sulphanyl-pyridine-3,5-dicarbonitrile are dissolved in 1 ml of DMF. 103 mg (1.23 mmol) of sodium bicarbonate and 75.4 mg (0.46 mmol) of 2-picolyl chloride hydrochloride are then added. The suspension is shaken at RT overnight, and water is added. The precipitate is filtered off with suction, washed with ethanol and diethyl ether and dried at 40° C. under reduced pressure. This gives 104 mg (81% of theory) of product.

MS (ESIpos): m/z=418 (M+H)$^+$ $^1$H=NMR (300 MHz, DMSO-d$_6$): δ=3.3 (s, 3H); 3.7 (tr, 2H); 4.2 (tr, 2H); 4.6 (s, 2H); 7.1 (d, 2H); 7.4 (dd, 1H); 7.45 (d, 2H); 7.65 (d, 1H); 7.75 (tr, 1H); 8.0 (s, broad, 2); 8.5 (d, 1H).

Example 8

2-Amino-4-[4-(2-methoxyethoxy)phenyl]-6-[(2-methyl-1,3-thiazol-4-yl)methyl -sulphanyl]pyridine-3,5-dicarbonitrile

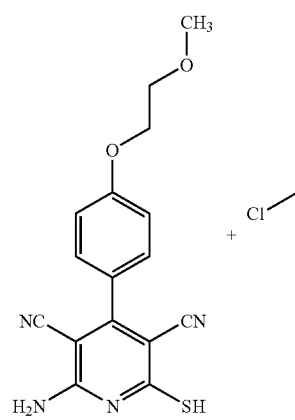

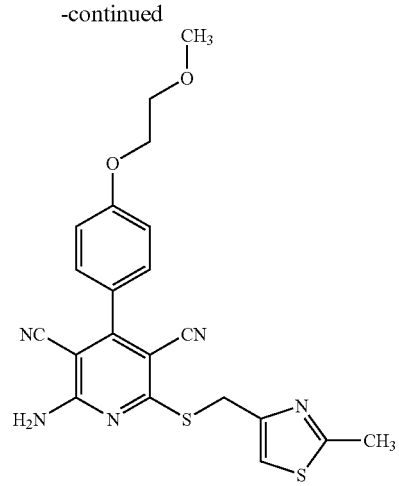

100 mg (0.31 mmol) of 2-amino-4-[4-(2-methoxyethoxy) phenyl]-6-sulphanyl-pyridine-3,5-dicarbonitrile are dissolved in 1 ml of DMF. 103 mg (1.23 mmol) of sodium bicarbonate and 90.5 mg (0.61 mmol) of 4-chloromethyl-2-methyl-1,3-thiazole are then added. The suspension is shaken at RT overnight, and water is added. The precipitate is filtered off with suction and dried at 40° C. under reduced pressure. This gives 88.8 mg (66.2% of theory) of product.

MS (ESIpos): m/z=438 (M+H)$^+$

Example 9

2-Amino-4-[4-(2-methoxyethoxy)phenyl]-6-[(2-amino-1,3-thiazol-4-yl)methyl-sulphanyl]pyridine-3,5-dicarbonitrile

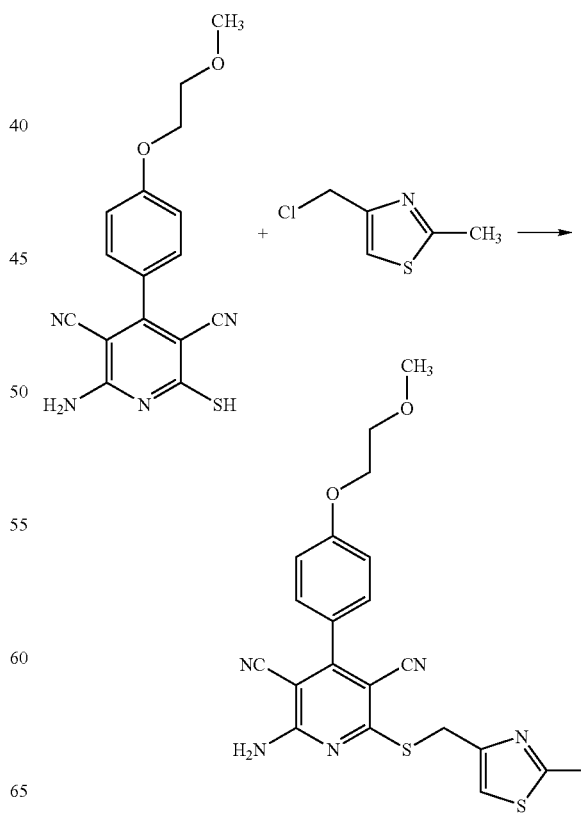

100 mg (0.31 mmol) of 2-amino-4-[4-(2-methoxyethoxy) phenyl]-6-sulphanyl-pyridine-3,5-dicarbonitrile are dissolved in 1 ml of DMF. 103 mg (1.23 mmol) of sodium bicarbonate and 68.3 mg (0.46 mmol) of 4-chloromethyl-2-amino-1,3-thiazole are then added. The suspension is shaken at RT overnight, and water is added. The precipitate is filtered off with suction, washed with ethanol and diethyl ether and dried at 40° C. under reduced pressure. This gives 115.9 mg (86.2% of theory) of product.

MS (ESIpos): m/z=439 (M+H)$^+$

Example 10

2-Amino-4-[4-(2-methoxyethoxy)phenyl]-6-[(2-(2-pyridyl)-1,3-thiazol-4-yl)methyl -sulphanyl]pyridine-3,5-dicarbonitrile

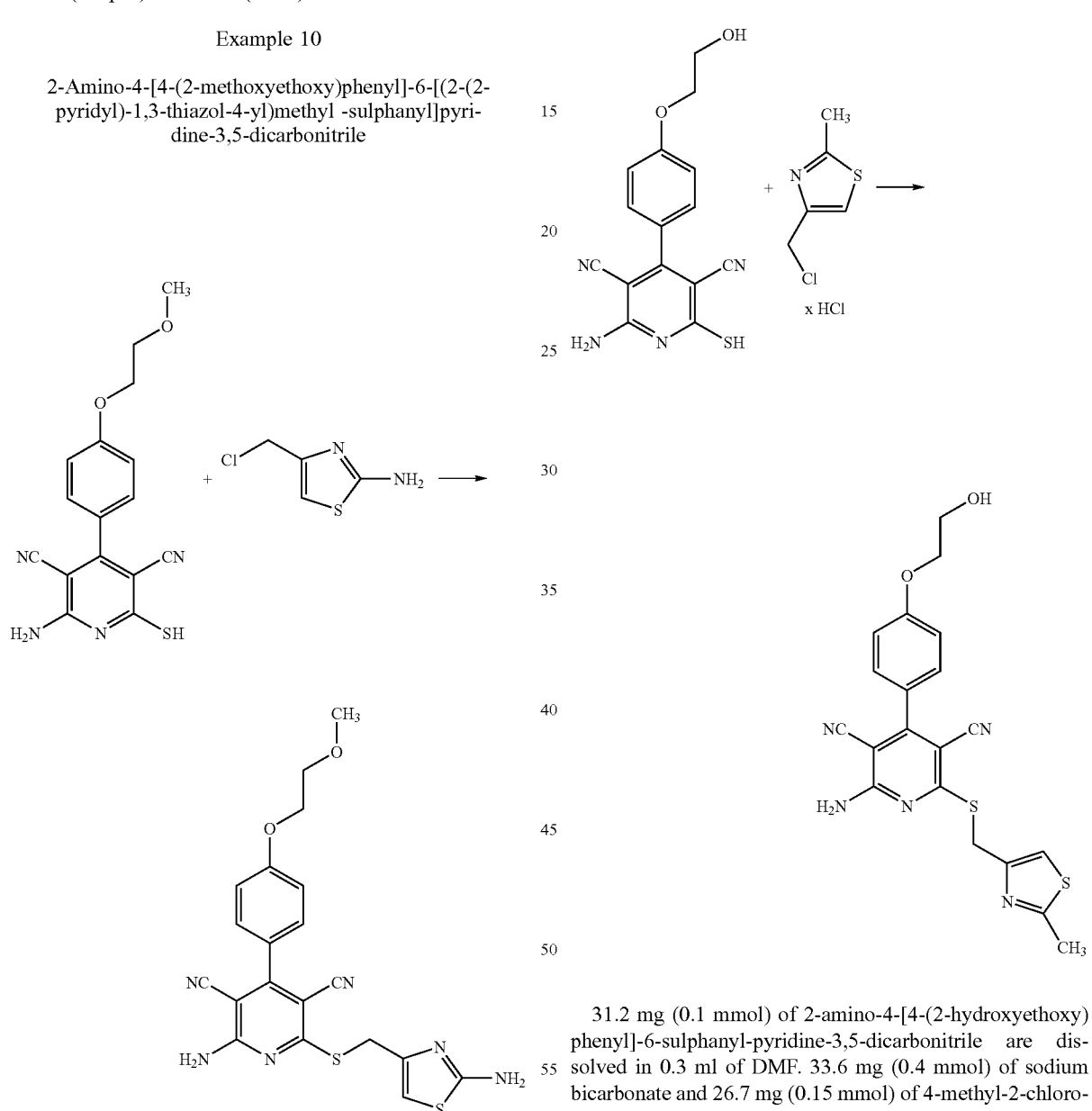

50 mg (0.15 mmol) of 2-amino-4-[4-(2-methoxyethoxy) phenyl]-6-sulphanyl-pyridine-3,5-dicarbonitrile are dissolved in 1 ml of DMF. 51.5 mg (0.61 mmol) of sodium bicarbonate and 58.6 mg (0.23 mmol) of 4-chloromethyl-2-(2-pyridyl)-1,3-thiazole are then added. The suspension is shaken RT overnight, and water is added. The precipitate is filtered off with suction, washed with ethanol and diethyl ether and dried at 40° C. under reduced pressure. This gives 67.4 mg (87.9% of theory) of product.

MS (ESIpos): m/z=501 (M+H)$^+$

Example 11

2-Amino-4-[4-(2-hydroxyethoxy)phenyl]-6-{[(2-methyl-1,3-thiazol-4-yl)methyl]-sulphanyl}pyridine-3,5-dicarbonitrile 31.2 mg (0.1 mmol) of 2-amino-4-[4-(2-hydroxyethoxy) phenyl]-6-sulphanyl-pyridine-3,5-dicarbonitrile are dissolved in 0.3 ml of DMF. 33.6 mg (0.4 mmol) of sodium bicarbonate and 26.7 mg (0.15 mmol) of 4-methyl-2-chloro-1,3-thiazole hydrochloride are then added. The suspension is shaken at RT overnight, filtered, and purified by preparative HPLC [column: Macherey-Nagel VP 50/21 Nucleosil 100-5 C18 Nautilus, 20×50 mm; flow rate: 25 ml/min; gradient (A=acetonitrile, B=water+0.3% trifluoroacetic acid): 0 min 10% A; 2.0 min 10% A; 6.0 min 90% A; 7.0 min 90% A; 7.1 min 10% A; 8.0 min 10% A; detection: 220 nm]. Concentration of the appropriate fraction gives 20.2 mg (47.7% of theory) of product.

MS (ESIpos): m/z=424 (M+H)$^+$

Example 12

2-Amino-6-{[(2-amino-1,3-thiazol-4-yl)methyl]sulphanyl}-4-[4-(2-hydroxyethoxy)-phenyl]pyridine-3,5-dicarbonitrile

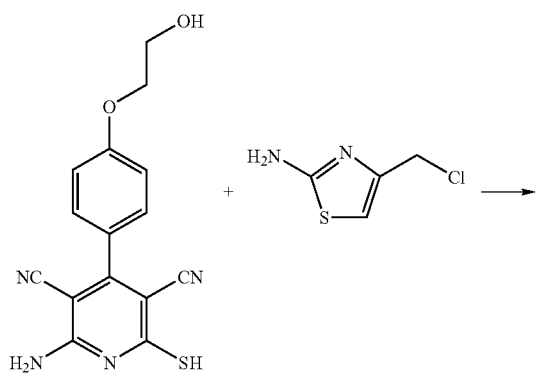

31.2 mg (0.1 mmol) of 2-amino-4-[4-(2-hydroxyethoxy)phenyl]-6-sulphanyl-pyridine-3,5-dicarbonitrile are dissolved in 0.3 ml of DMF. 33.6 mg (0.4 mmol) of sodium bicarbonate and 22.3 mg (0.15 mmol) of 4-amino-2-chloro-1,3-thiazole are then added. The suspension is shaken at RT overnight, filtered, and purified by preparative HPLC [column: Macherey-Nagel VP 50/21 Nucleosil 100-5 C18 Nautilus, 20×50 mm; flow rate: 25 ml/min; gradient (A=acetonitrile, B=water+0.3% trifluoroacetic acid): 0 min 10% A; 2.0 min 10% A; 6.0 min 90% A; 7.0 min 90% A; 7.1 min 10% A; 8.0 min 10% A; detection: 220 nm]. Concentration of the appropriate fraction gives 35.7 mg (84.1% of theory) of product.

MS (ESIpos): m/z=425 (M+H)⁺

Example 13

2-Amino-4-[4-(2-methoxyethoxy)phenyl]-6-({[2-(4-morpholinyl)-1,3-thiazol-4-yl]-methyl}sulphanyl)pyridine-3,5-dicarbonitrile Step 1:

4-[4-(Chloromethyl)-1,3-thiazol-2-yl]morpholine

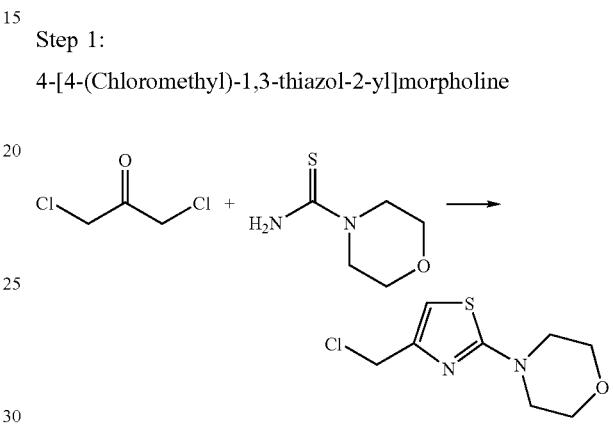

11.51 g (78.76 mmol) of 4-morpholinecarbothioamide and 10.00 g (78.76 mmol) of dichloroacetone in 100 ml of ethanol are heated under reflux for one hour. The colourless solid which precipitates from the pink solution is, after cooling, filtered off with suction and washed twice with ethanol. This gives 12.96 g (75% of theory) of product.

MS (ESIpos): m/z=219 (M+H)⁺

Step 2:

2-Amino-4-[4-(2-methoxyethoxy)phenyl]-6-({[2-(4-morpholinyl)-1,3-thiazol-4-yl]-methyl}sulphanyl)pyridine-3,5-dicarbonitrile

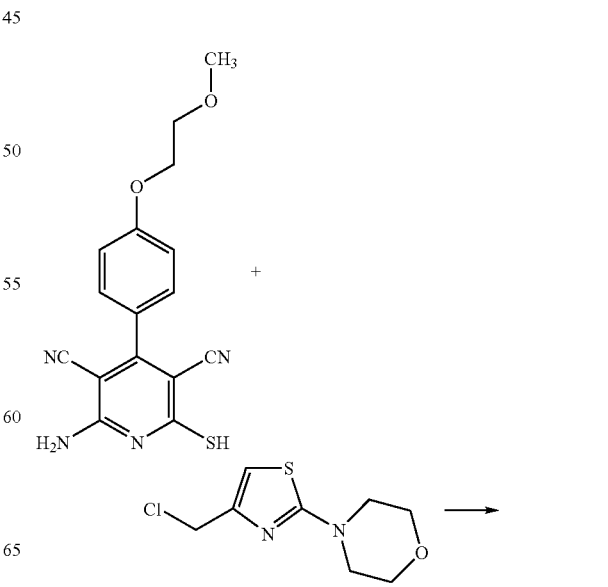

-continued

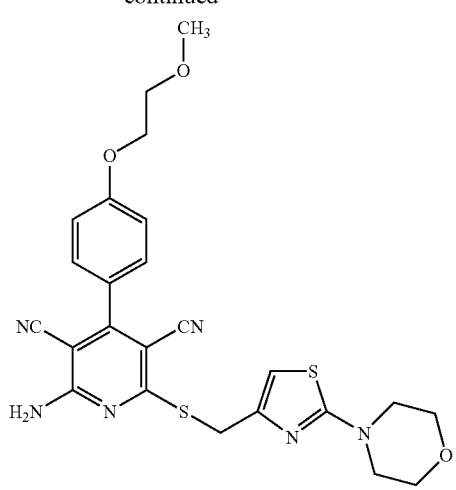

2 g (6.13 mmol) of 2-amino-4-[4-(2-methoxyethoxy)phenyl]-6-sulphanylpyridine-3,5-dicarbonitrile and 2.68 g (12.26 mmol) of 4-(4-(chloromethyl)-1,3-thiazol-2-yl]morpholine are dissolved in dry DMF (50 ml), and 1.83 ml (12.26 mmol) of DBU are added. After 3 hours of stirring at RT, the solvent is removed using a rotary evaporator and the residue is purified by preparative HPLC (column: Kromasil 100 C18 250×20 mm, 10 μm; acetonitrile/water gradient: 3 minutes of 10% acetonitrile which is then, over a period of 30 minutes, increased to 80% acetonitrile; flow rate: 25 ml/min). This gives 1.70 g (55% of theory) of product.

MS (ESIpos): m/z=509 (M+H)$^+$ $^1$H-NMR (300 MHz, DMSO-d$_6$): δ=3.3 (m, 7H); 3.7 (m, 6H); 4.2 (tr, 2H); 4.4 (s, 2H); 6.95 (s, 1H); 7.15 (d, 2H); 7.45 (d, 2H); 8.0 (s, broad, 2H).

The examples listed in Table 3 were prepared analogously to Example 13. The chloromethylthiazoles used as starting materials are either commercially available or can be prepared analogously to step 1 in Example 13.

TABLE 3

| Example No. | Structure | Expected molar mass | [M + H]$^+$ found |
|---|---|---|---|
| 14 | 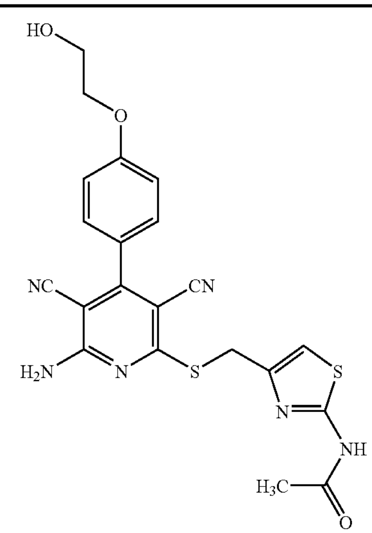 | 467 | 468 |
| 15 | 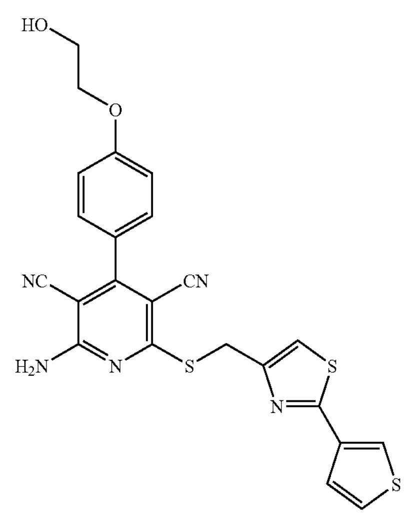 | 492 | 493 |

TABLE 3-continued

| Example No. | Structure | Expected molar mass | [M + H]+ found |
|---|---|---|---|
| 16 | 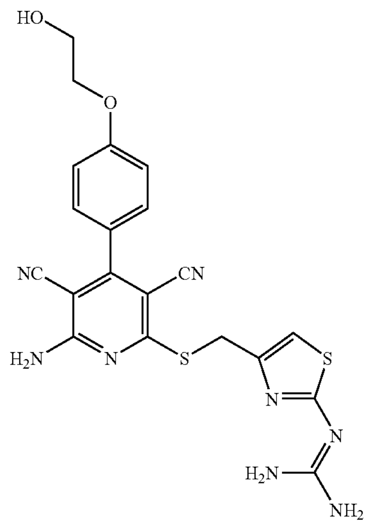 | 467 | 468 |
| 17 | 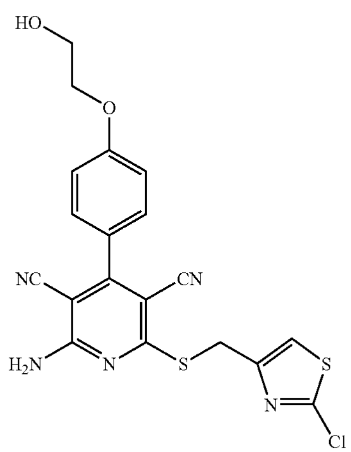 | 444 | 445 |
| 18 | 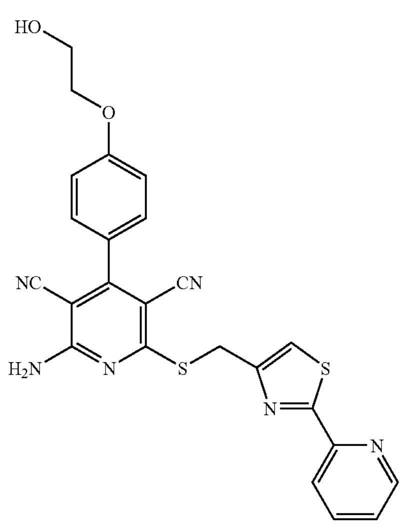 | 487 | 488 |

TABLE 3-continued
| Example No. | Structure | Expected molar mass | [M + H]+ found |
|---|---|---|---|
| 19 | 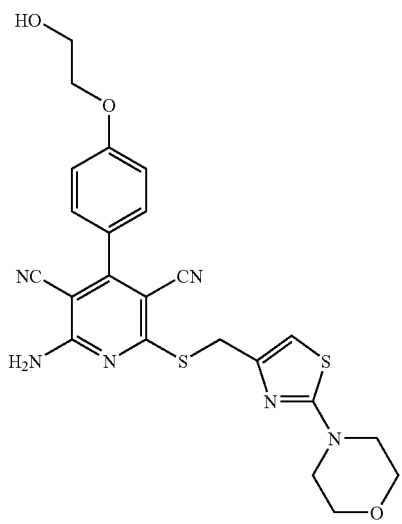 | 495 | 496 |
| 20 | 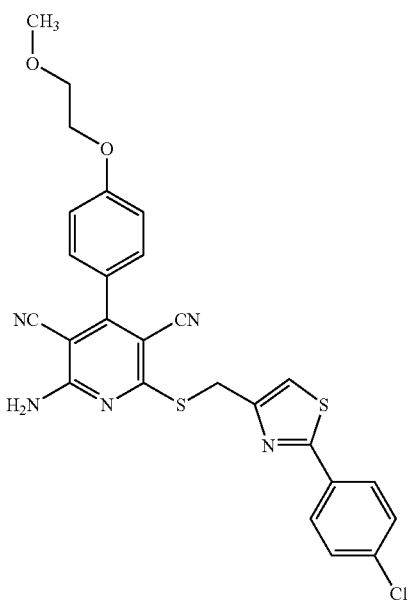 | 534 | 535 |

TABLE 3-continued
| Example No. | Structure | Expected molar mass | [M + H]+ found |
|---|---|---|---|
| 21 | 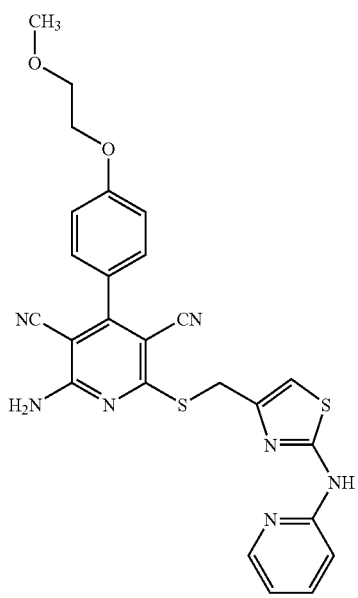 | 516 | 517 |
| 22 | 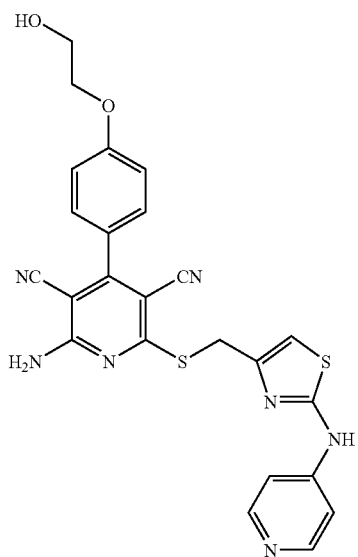 | 502 | 503 |

TABLE 3-continued
| Example No. | Structure | Expected molar mass | [M + H]+ found |
|---|---|---|---|
| 23 | 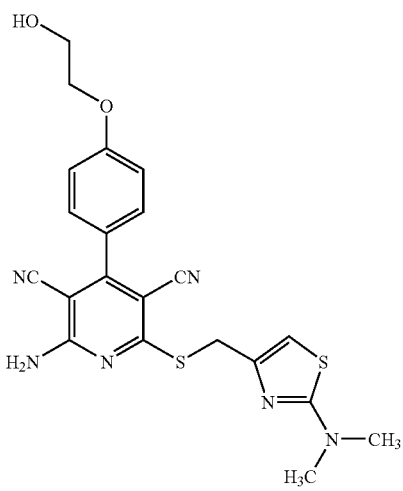 | 453 | 454 |
| 24 | 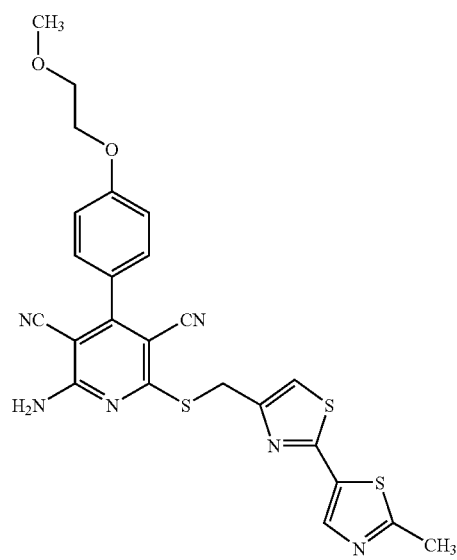 | 521 | 522 |

TABLE 3-continued
| Example No. | Structure | Expected molar mass | [M + H]+ found |
|---|---|---|---|
| 25 | 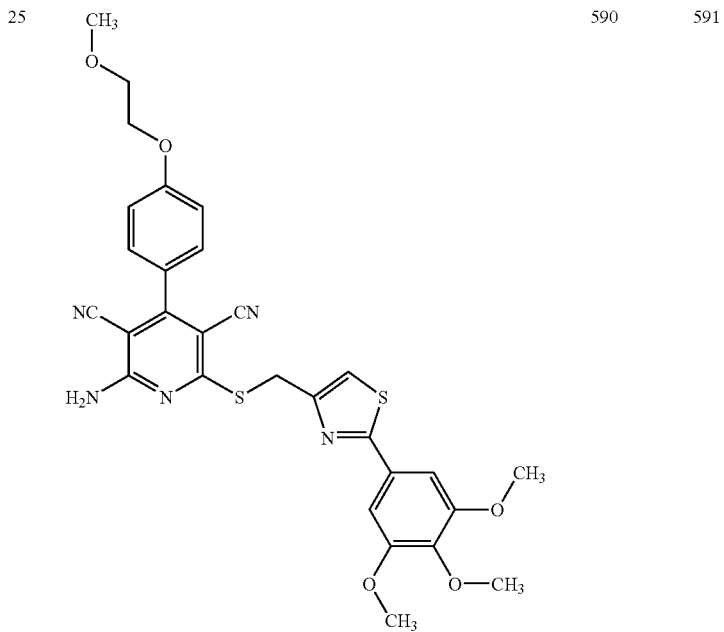 | 590 | 591 |
| 26 | 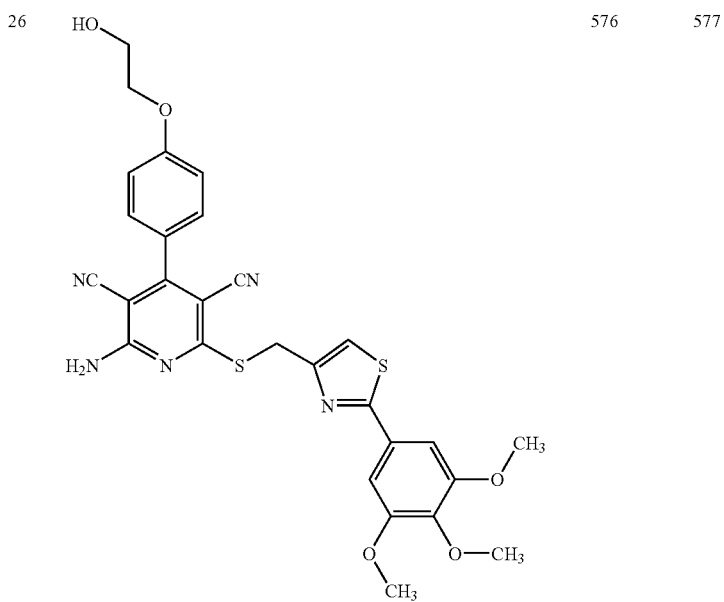 | 576 | 577 |

TABLE 3-continued

| Example No. | Structure | Expected molar mass | [M + H]+ found |
|---|---|---|---|
| 27 | 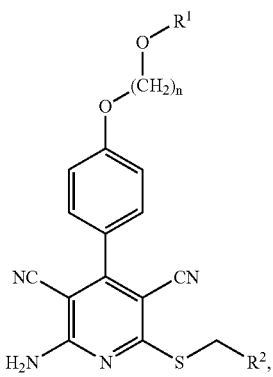 | 467 | 468 |

The invention claimed is:

1. A compound of the formula (I)

(I)

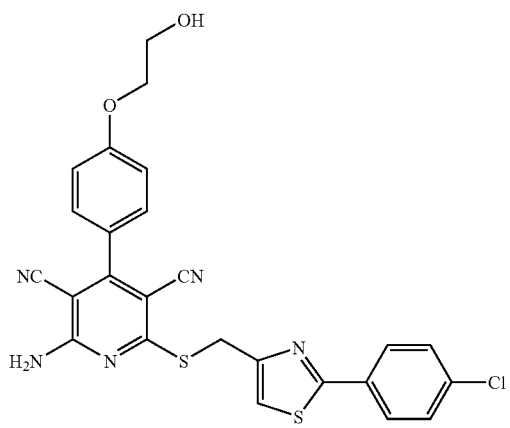

in which n represents a number 2, 3 or 4, $R^1$ represents hydrogen or $(C_1-C_4)$-alkyl and $R^2$ represents pyridyl or thiazolyl which for its part may be substituted by $(C_1-C_4)$-alkyl, halogen, amino, dimethylamino, acetylamino, guanidino, pyridylamino, thienyl, furyl, imidazolyl, pyridyl, morpholinyl, thiomorpholinyl, piperidinyl, piperazinyl, N-$(C_1-C_4)$-alkylpiperazinyl, pyrrolidinyl, oxazolyl, isoxazolyl, pyrimidinyl, pyrazinyl, optionally $(C_1-C_4)$-alkyl-substituted thiazolyl or phenyl which is optionally substituted up to three times by halogen, $(C_1-C_4)$-alkyl or $(C_1-C_4)$-alkoxy, or a pharmaceutically acceptable salt, hydrate, hydrate of a salt, or solvate thereof.

2. The compound of the formula (I) according to claim 1, in which n represents the number 2, $R^1$ represents hydrogen, methyl or ethyl, and $R^2$ represents pyridyl or thiazolyl which for its part may be substituted by methyl, ethyl, fluorine, chlorine, amino, dimethylamino, acetylamino, guanidino, 2-pyridylamino, 4-pyridylamino, thienyl, pyridyl, morpholinyl, piperidinyl, optionally methyl-substituted thiazolyl or phenyl which is optionally substituted up to three times by chlorine or methoxy, or a pharmaceutically acceptable salt, hydrate, hydrate of a salt, or solvate thereof.

3. The compound of the formula (I) according to claim 1, in which n represents the number 2, $R^1$ represents hydrogen or methyl and $R^2$ represents pyridyl or thiazolyl which for its part may be substituted by methyl, chlorine, amino, dimethylamino, acetylamino, guanidino, 2-pyridylamino, 4-pyridylamino, thienyl, pyridyl, morpholinyl, 2-methylthiazol-5-yl, phenyl, 4-chlorophenyl or 3,4,5-trimethoxyphenyl, or a pharmaceutically acceptable salt, hydrate, hydrate of a salt, or solvate thereof.

4. The compound according to claim 1 having the following structure or a pharmaceutically acceptable salt, hydrate, hydrate of a salt, or solvate thereof.

5. Process for preparing compounds of the formula (I) as defined in claim 1, characterized in that compounds of the formula (II)

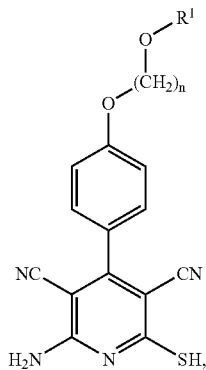

in which n and $R^1$ are as defined in claim 1, are reacted with compounds of the formula (III)

$$R^2\text{—}CH_2\text{-}X \qquad (III),$$

in which $R^2$ is as defined in claim 1 and X represents a leaving group.

6. A pharmaceutical composition, comprising at least one compound of the formula (I) as defined in claim 1 and at least one auxiliary.

7. A pharmaceutical composition, comprising at least one compound of the formula (I) as defined in claim 1 and at least one further active compound.

8. A method of treating disorders of the cardiovascular system, comprising administering to a patient in need thereof an effective amount of a compound of formula (I) as defined in claim 1.

* * * * *